United States Patent
Yamada

[11] 3,971,386
[45] July 27, 1976

[54] THORN TWEEZERS

[76] Inventor: Masayoshi Yamada, 39, Sengencho 1-chome, Shizuokashi, Shizuoka, Japan

[22] Filed: Sept. 9, 1974

[21] Appl. No.: 504,403

[30] Foreign Application Priority Data
Sept. 11, 1973  Japan............................... 48-102461
Feb. 16, 1974  Japan............................... 49-18893

[52] U.S. Cl. ............................................. 128/354
[51] Int. Cl.² ......................................... A61B 17/30
[58] Field of Search ............ 128/314, 329, 330, 354

[56] References Cited
UNITED STATES PATENTS
1,433,340  10/1922  Clark ................................. 128/354
1,667,170  4/1928  Segal.................................. 128/354
2,442,416  6/1948  Kulicke, Jr. et al. ............. 128/329 X FOREIGN PATENTS OR APPLICATIONS
567,627  12/1923  France............................... 128/314

*Primary Examiner*—Channing L. Pace
*Attorney, Agent, or Firm*—Frank J. Jordan

[57] ABSTRACT

A thorn tweezer includes a generally U-shaped member, mounting means on the U-shaped member, and a needle slidable in the mounting means between an extended position in which the needle extends beyond the U-shaped member to facilitate dislodging of a thorn or splinter and to a retracted position in which the needle is safely retained within the U-shaped member.

1 Claim, 22 Drawing Figures

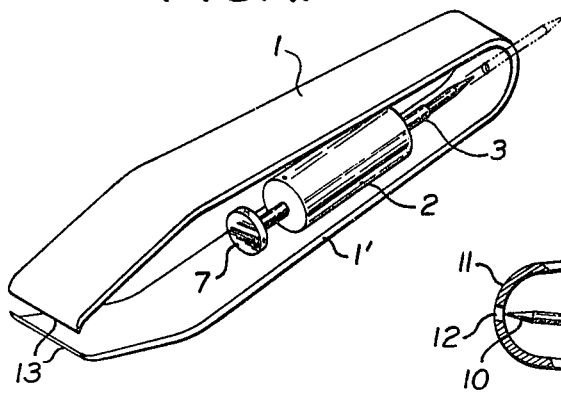
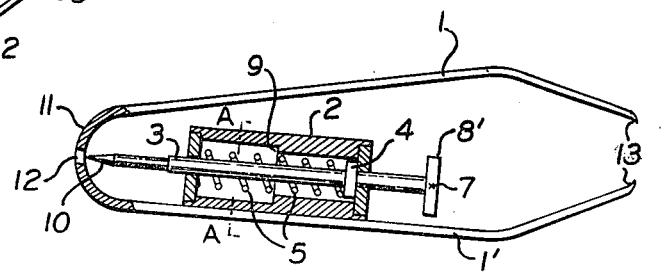
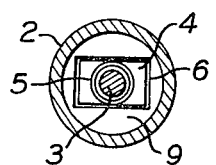
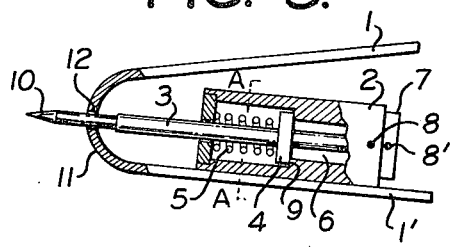
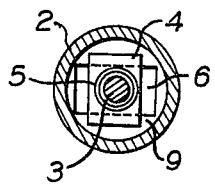
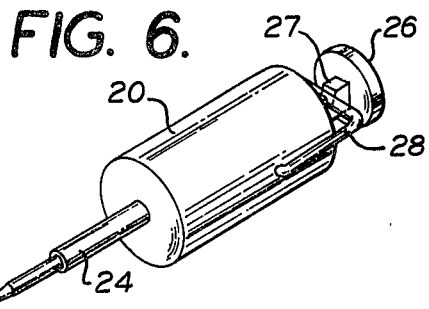
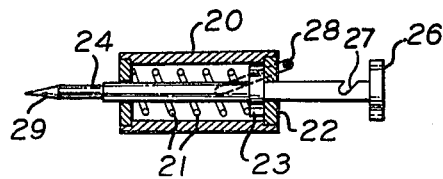
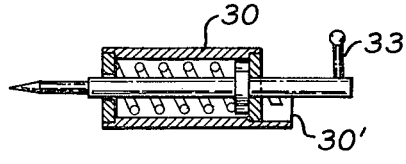
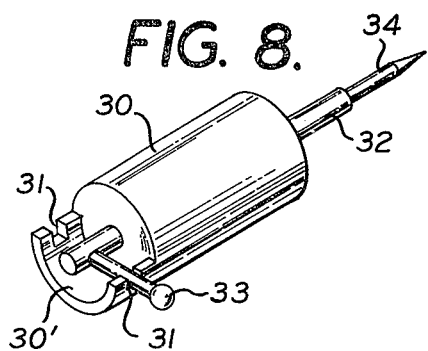

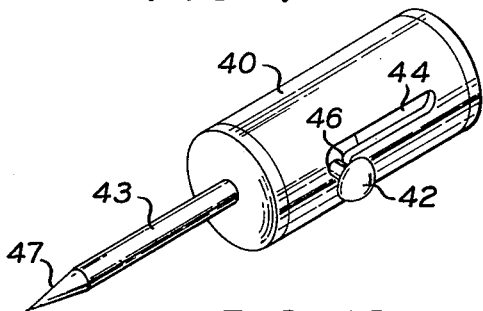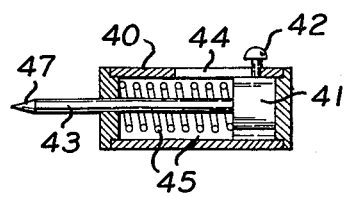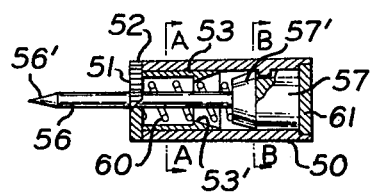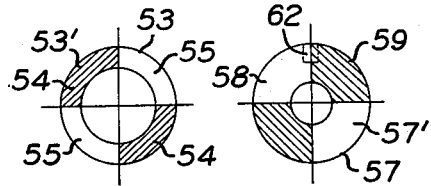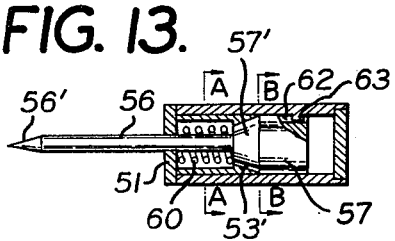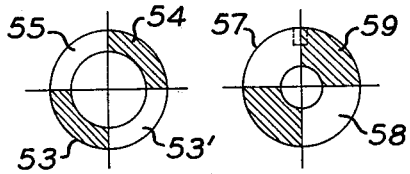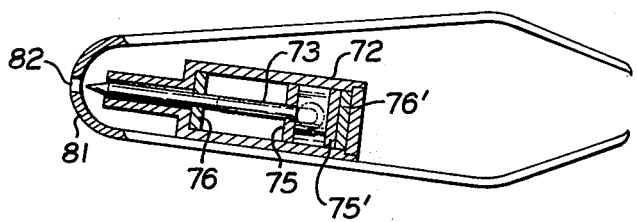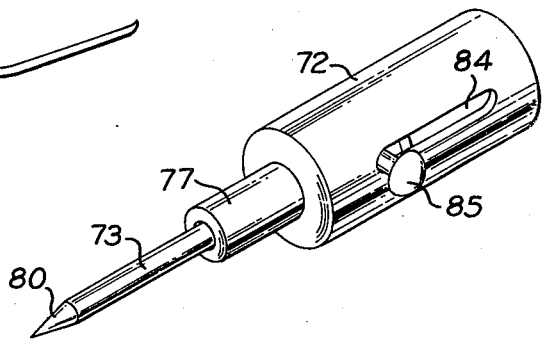

3,971,386

THORN TWEEZERS

BACKGROUND OF THE INVENTION

This invention relates to thorn tweezers for removing thorns, splinters or the like from the fingers, legs or other parts of the body.

Heretofore, a needle and a tweezer have been used separately for removing thorns and splinters from the hands, legs or other parts of the body. Since the needle is very slender and also since the tweezer is also very small, such articles are difficult to locate when they are needed quickly. Frequently these small articles are stored in locations with other items and because of their small size, it is difficult to locate them amongst the various other larger items. Accordingly, when it is desired to locate a needle or tweezers in a hurry to remove a splinter or thorn, they are not always readily available nor can they be found quickly as may be desired. As a result, it might not be possible to remove a thorn or splinter quickly which could result in inflammation of the flesh which in turn may cause or result in serious injury.

Accordingly, an object of the present invention is to overcome the disadvantages of known prior art arrangements and to avoid the aforementioned inconveniences by providing tweezers on which a needle is slidably mounted. The needle is slidable to a retracted position in which the needle is safely retained between the shanks of the tweezer. When it is desired to use the needle, the latter may be slid into an extended or operative position wherein the needle extends beyond the tweezer where it may be used to facilitate dislodging and loosening the thorn or splinter from the flesh. Once the thorn or splinter has been dislodged or exposed, the tweezer may be readily utilized to remove the thorn or splinter.

Other features which are considered characteristic of the invention are set forth in the appended claims.

Although the invention is illustrated and described in relationship to specific embodiments, it is nevertheless not intended to be limited to the details shown, since various modifications and structural changes may be made therein without departing from the spirit of the invention and within the scope and range of equivalents of the claims.

The construction and operation of the invention, however, together with additional objects and advantages thereof will be best understood from the following description of specific embodiments when read in connection with the accompanying drawings.

SUMMARY OF THE INVENTION

A thorn tweezer includes a generally U-shaped member, mounting means on the U-shaped member, and a needle slidable in the mounting means between an extended position in which the needle extends beyond the U-shaped member to facilitate dislodging of a thorn or splinter and to a retracted position in which the needle is safely retained within the U-shaped member.

BRIEF DESCRIPTION OF THE DRAWINGS

FIG. 1 is a perspective view of a thorn tweezer according to a first embodiment of the present invention.

FIG. 2 is a longitudinal section view of the thorn tweezer shown in FIG. 1.

FIG. 3 is a partial longitudinal sectional view similar to FIG. 2 but showing the needle in an extended position.

FIG. 4 is a sectional view taken along the line A-A in FIG. 2.

FIG. 5 is a sectional view taken along the line A-A in FIG. 3.

FIG. 6 is a perspective view of a thorn tweezer according to a second embodiment.

FIG. 7 is a longitudinal sectional view of the thorn tweezer shown in FIG. 6.

FIG. 8 is a perspective view of a thorn tweezer according to a third embodiment.

FIG. 9 is a longitudinal sectional view of the thorn tweezer shown in FIG. 8.

FIG. 10 is a perspective view of a thorn tweezer according to a fourth embodiment.

FIG. 11 is a longitudinal sectional view of the thorn tweezer shown in FIG. 10.

FIG. 12 is a longitudinal sectional view of a cylinder and a needle arrangement according to a fifth embodiment.

FIG. 13 is a longitudinal sectional view similar to FIG. 12 but showing the needle in an extended position.

FIG. 14 is a partial and schematic sectional view of the sleeve magnets used in FIG. 12 and taken generally along the line A-A in FIG. 12.

FIG. 15 is a partial and schematic sectional view of the sleeve magnets used in FIG. 13 and taken generally along the line A-A in FIG. 13.

FIG. 16 is a partial and schematic view of the piston magnets used in FIG. 12 and taken generally along the line B-B in FIG. 12.

FIG. 17 is a partial and schematic sectional view of the piston magnets used in FIG. 13 and taken generally along the line B-B in FIG. 13.

FIG. 18 is a longitudinal sectional view of a thorn tweezer according to a sixth embodiment.

FIG. 19 is a perspective view of the thorn tweezer shown in FIG. 18.

DESCRIPTION OF THE PREFERRED EMBODIMENTS

Figure 20:
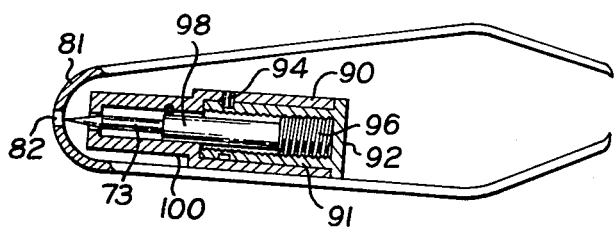
FIG. 20 is a longitudinal sectional view of a thorn tweezer according to a seventh embodiment.

Referring to the drawings and particularly to the first embodiment shown in FIGS. 1 to 5, a U-shaped member 1 includes a pair of shanks 1'. The shanks 1' are integrally adjoined at one end in U-shaped fashion while the terminating ends define opposed ends 13. Disposed on the inner face of the shanks 1' is a small cylinder 2 which is closed at both ends. A needle 3 passes through both longitudinal ends of the cylinder 2 and has mounted thereon a rectangular flange 4. The flange 4 which is movably insertable in a groove 6 in the cylinder 2 also has a rectangular configuration. A spring 5 is located within the cylinder around the needle 3, the arrangement being such that the spring 5 bears against the rectangular flange 4 and biases the needle 3 to its retracted position as shown in FIG. 2. The needle 3 has a flange or button 7 affixed at the projecting rear end and this button 7 is provided with a mark 8' which is adapted to align with a mark 8 on the cylinder 6 to indicate the rotational position of the button 7 relative to the cylinder 2. As best can be seen in FIG. 2, the groove 6 terminates at a step 9 within the cylinder 2.

From the above description, it can be seen that the button 7 may be grasped with the fingers in order to extend the needle to the position shown in FIG. 3 as the rectangular flange 4 slides within its corresponding groove 6 in the cylinder 2. Thus the needle may be readily extended against the bias of spring 5 until the flange 4 reaches the step 9 within the cylinder 2 whereupon the needle may be rotated 90° or so as shown in FIG. 5, so that the rectangular flange 4 engages the step 9 on the cylinder 2 to thereby retain the needle in the extended position as shown in FIG. 3. In the extended position, the needle point 10 projects outwardly of the U-shaped member 1, passing through a slot 12 at the curved root or U-shaped end portion 11 of the U-shaped member. With the needle retained in its extended position, the needle point 10 is useful to facilitate dislodging or removal of a thorn or splinter from the flesh. This is effected by holding the shanks 1' by the fingers and after manipulating the needle to dislodge or loosen the thorn or splinter, the position of the tweezer may be reversed in the user's hand whereupon the shanks 1' may thereafter be compressed so that the ends 13 may easily grasp the thorn or splinter end to readily pull it out of the flesh without difficulty.

After use the button 7 may be rotated so that the marks 8,8' are in longitudinal alignment. When this occurs, the rectangular flange 4 is aligned with the rectangular groove 6 and the spring 5 thereby bears against the flange 4 to move the needle into the withdrawn position as shown in FIG. 2, whereby the needle point 10 is safely disposed within the end 11.

With the above described arrangement it can be seen that the needle may be safely and inseparably retained within the tweezer so as to provide a complete thorn tweezer which is provided with a needle which may be extended and retracted for use as desired.

In the second embodiment of the present invention as shown in FIGS. 6 and 7, the needle 24 is provided with a flange 23 which is biased against an end plate 22 of the cylinder 20 by means of a spring 21 disposed in the cylinder. The needle is provided with a hook portion 27 at its projecting end, the latter also being provided with a flange or button 26. A ring 28 is pivotally mounted on diametrically opposed portions of the surface of the cylinder 20 and this ring 28 is pivotally engagable with the hook portion 27 on the needle so as to retain the needle point 29 in its extended position, whereby the needle point 29 projects through a slot or opening in the U-shaped portion of the tweezer. The retracted position of the needle is shown in FIG. 7 whereas the extended position is shown in FIG. 6.

According to a third embodiment of the present invention as shown in FIGS. 8 and 9, a lever 33 is affixedly secured to the needle 32 and projects laterally from the latter. The lever 33 is adapted to removably engage the grooves 31 disposed in the rear extension 30' of the cylinder 30. Thus it will be seen in FIG. 8 that the needle may be rotated so that the lever 33 engages either one of the grooves 31 to retain the needle in its extended position. The retracted position of the needle is shown in FIG. 9. Here again, the needle point 34 passes through an opening in the U-shaped end of the tweezer as in the previous embodiments. Also a spring and flange on the needle are provided as in the prior embodiments.

According to a fourth embodiment as shown in FIGS. 10 and 11, a cylinder 40 is provided with a piston 41 fixedly mounted on the end of the needle 43. The piston 41 is provided with a lever 42 and the piston is biased in its retracted position by a spring 45. The lever 42 is adapted to slide in a longitudinal groove 44. However, the longitudinal end of the groove 44 is provided with a side slot 46 such that when the needle is moved to its extended position, the lever 42 may be shifted laterally to engage the side slot 46 to thereby retain the needle in its projected position wherein the needle point 47 projects out of the U-shaped portion of the tweezers.

In a fifth embodiment shown in FIGS. 12 to 17, a cylinder 50 is provided with a sleeve 53 rotatable within the cylinder 50. An end plate 51 provided at the longitudinal end of the sleeve 53 defines the end of the cylinder 50. The end plate 51 may be provided with a peripheral roughness such as knurling or the like. At the opposite end of the sleeve 53 there is provided a tapered end portion 53' which is peripherally tapered on the inside. The tapered portion 53' is provided with four adjacent, arc-shaped sections forming magnets of opposite magnetic polarity arranged alternately to one another as indicated by the numerals 53 and 54 in FIG. 14.

A needle 56 disposed within the cylinder 50 has a piston 57 fixed at one end thereof and this piston 57 has a tapered head 57' which also comprises four adjacent, arc-shaped sections of magnetic material having opposite and alternately arranged magnetic polarity as indicated at 58 and 59 in FIG. 16. The piston 57 is normally biased by a spring 80 in the cylinder to urge the needle 56 to its retracted position as shown in FIG. 12.

From the above description, it can be seen that by grasping the end plate 51 with the fingers, the sleeve 53 may be rotated in the cylinder 50 so as to cause the magnetic sections 54, 55 to longitudinally align themselves with the magnetic sections 58, 59 of the piston head 57'. Since the magnetic polarity of the aforementioned magnetic sections are of opposite polarity relative to each other, the result is that the piston 57 is caused to be extended to the position shown in FIG. 13 as a result of the attraction of the opposite magnets. When this occurs, the piston 57 slides from the position shown in FIG. 12 to the position shown in FIG. 13. A projection 63 extending from the inner side wall of the cylinder engages a groove 62 in the piston so as to prevent rotation of the piston as the latter slides within the cylinder. When the needle point 56' is extended, it projects beyond the U-shaped portion of the tweezers as in the previous embodiment so as to facilitate removal of a splinter and/or thorn.

When the end plate 51 is rotated progressively or reversedly and the sleeve is rotated so that the magnetic portions thereon are rotated relative to the previously described position, the piston will return to its non-extended position against the end plate 61 as shown in FIG. 13 due to the magnetic repulsion between longitudinally aligned and opposed magnets as well as due to the bias of the spring 60 so as to place the needle point 56' within the U-shaped member as in the prior embodiments.

In a sixth embodiment of the present invention as shown in FIGS. 18 and 19, a cylinder 72 is provided with a tubular guide 77 disposed within the U-shaped member. At both longitudinal ends of the cylinder 72 there are provided end plates which at the inner faces are provided with a pair of magnets 76, 76'. At the same time, a pair of magnetic elements 75, 75' are affixed to opposite ends of a piston 74 which is slidably mounted in the cylinder 72. A pin 85 is fixed to the piston 74 and extends laterally outwardly through a groove 84 in the side wall of the cylinder. The pin 85 may be manually pushed forwardly or backwardly to determine the extended or non-extended position of the needle.

When the piston 74 is positioned at its rear end in the cylinder 72, it will be retained in this position by the magnetic attraction of the magnet 76' and the magnetic element 75'. When pushed to its extended position, by grasping the pin 85 with the finger, the needle will be retained in its extended position by the magnetic attraction between the magnetic element 75 and the magnet 76. In the extended position, the needle point 80 projects beyond the U-shaped portion of the tweezers.

The magnetic attraction between the magnet 76 and the magnetic element 75 is sufficient to retain the needle in its extended position as the needle is used to dislodge a splinter or thorn. At the same time, deep penetration into the flesh is avoided because if the pressure applied is too great the magnetic attraction is overcome. Accordingly, heavy loads applied to the needle will cause it to be retracted within the nipper safely, easily and rapidly.

Figure 21:
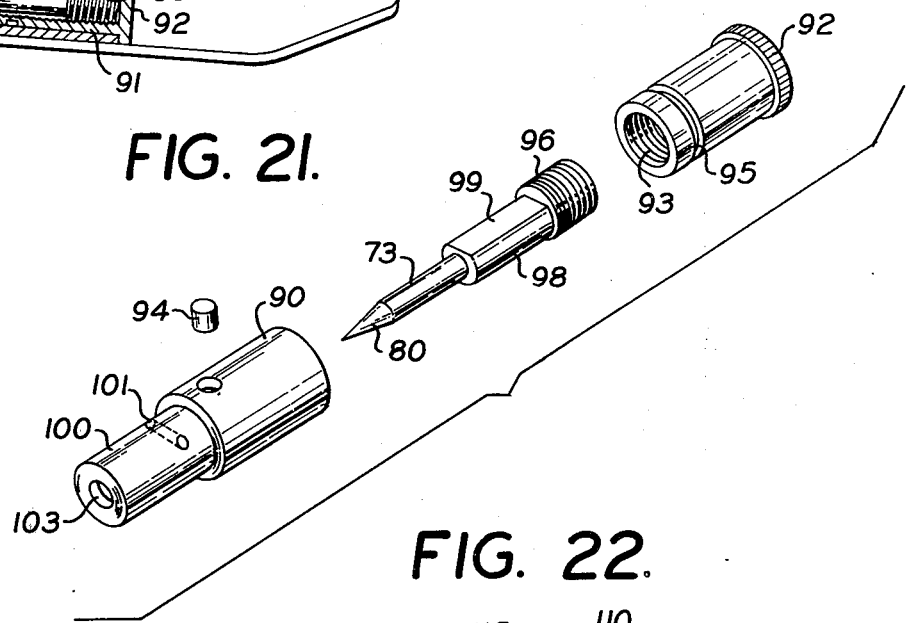
FIG. 21 is an exploded view of the thorn tweezer shown in FIG. 20.

According to a seventh embodiment as shown in FIGS. 20 and 21, a point 80 of the needle 73 may be adjustably positioned as regards the extent it projects beyond the U-shaped portion of the tweezers. In this embodiment, a cylinder 90 is provided with a sleeve 91 which is rotatably mounted within the cylinder 90 and which is provided with a knob 92 fitted at the longitudinal end thereof. A pin 94 projects from the cylinder 90 and is accommodated in a circular groove 95 formed on the surface of the sleeve 91. A guiding rod 98 is provided with a longitudinally extending flat surface 99 and this guiding rod 98 is affixed to the end of the needle 73. The guiding rod 98 has a threaded end 96 which threadedly engages internal thread 93 on the sleeve 91. The rod 98 is slidably mounted in a tubular guide 100 and the flat surface 99 is adapted to contact a transverse guiding pin 101 fixed transversely in the guide 100. The needle 73 on the front of the rod 98 projects through the opening 103 of the guide 100 and through an opening 82 in the U-shaped portion of the tweezers.

From the above description it will be seen that as the knob 92 is rotated, the sleeve 91 will rotate so that the threaded end 96 of the rod engages the inside threads 93 of the sleeve 91 to longitudinally advance or retract the needle 73. The contact between the flat surface 99 of the rod 98 and the pin 101 prevents rotation of the needle and rod 98. The needle point 80 may be projected any desired distance relative to the U-shaped portion 81 of the tweezer by rotating the sleeve 91 to the extent desired. In the case where a thorn is deeply embedded in the flesh, the needle may be easily projected the desired distance from the U-shaped portion 81 of the tweezer. Also the needle may be safely and harmlessly disposed in the tweezer so that it does not project therebeyond by turning the knob 92.

Figure 22:
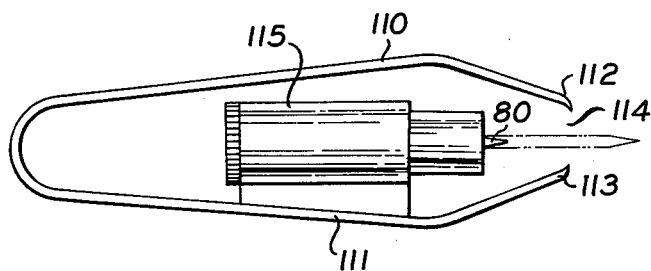
FIG. 22 is an elevational view of a thorn tweezer according to an eighth embodiment.

According to an eighth embodiment as shown in FIG. 22, a cylinder 115 may be fixed to the inside of the shank 111 in such a position that the needle point 80 may project through the opening 114 between the ends 112, 113 of the shanks 110,111. With this arrangement, the tweezer may be handled speedily and easily without changing or alternating the longitudinal position in which the tweezer is held by the hand because the needle point 80 projects and retracts at the same longitudinal end of the tweezers corresponding to the ends 112, 113 of the tweezers.

It is thought that the invention and many of its attendant advantages will be understood from the foregoing description and that it will be apparent that various changes may be made in the form, construction, and arrangements of the parts without departing from the spirit and scope of the invention or sacrificing all of its material advantages. The form heretofore described being merely a preferred embodiment thereof.

What is claimed is:

1. A thorn tweezer comprising an elongated resilient U-shaped member having a generally U-shaped end portion and a pair of opposed elongated shanks extending from said U-shaped end portion, said U-shaped end portion having an opening, said shanks having opposed terminating ends, said shanks being adapted to be manually compressed to move said opposed terminating ends towards one another to thereby grasp a thorn or splinter disposed therebetween, each of said shanks having an inner face which face opposite one another, a cylinder fixedly mounted on the inner face of one of said shanks such that said cylinder is disposed between said pair of elongated shanks, a needle having a point, means slidably mounting said needle in said cylinder for movement between an extended position in which the point of said needle extends beyond said U-shaped end portion of said resilient U-shaped member and a retracted position wherein the point of said needle is disposed within the longitudinal ends of said resilient U-shaped member, said needle passing through said opening in said U-shaped end portion when said needle is in said extended position, a laterally extending lever on said needle, a spring in said cylinder urging said needle into its retracted position, means on said cylinder adapted to be engaged by said lever to retain said needle in said extended position, said needle when in said extended position being operable to effect removal of a thorn or splinter from a person's body as the resilient U-shaped member functions as a handle to facilitate manipulation of said needle, said needle when in said retracted position being protected by said resilient U-shaped member to prevent injuries, said shanks of said resilient U-shaped member being adapted to be grasped by a user to move said terminating ends closer to one another independently of the movement of said needle between its retracted and extended positions, whereby the operation of said resilient U-shaped member and the operation of extending retracting said needle may be effected independently.

* * * * *